(12) United States Patent
Andersen et al.

(10) Patent No.: US 7,618,446 B2
(45) Date of Patent: *Nov. 17, 2009

(54) VALVE PROSTHESIS FOR IMPLANTATION IN THE BODY AND A CATHETER FOR IMPLANTING SUCH VALVE PROSTHESIS

(75) Inventors: Henning Rud Andersen, Hoejbjerg (DK); John Michael Hasenkam, Aarhus (DK); Lars Lyhne Knudsen, Aarhus (DK)

(73) Assignee: Edwards Lifesciences AG, Nyon (CH)

( * ) Notice: Subject to any disclaimer, the term of this patent is extended or adjusted under 35 U.S.C. 154(b) by 0 days.

This patent is subject to a terminal disclaimer.

(21) Appl. No.: 10/268,253

(22) Filed: Oct. 10, 2002

(65) Prior Publication Data

US 2003/0036795 A1 Feb. 20, 2003

Related U.S. Application Data

(60) Continuation of application No. 09/514,426, filed on Feb. 28, 2000, now Pat. No. 6,582,462, which is a continuation of application No. 09/026,574, filed on Feb. 20, 1998, now Pat. No. 6,168,614, which is a continuation of application No. 08/955,228, filed on Oct. 21, 1997, now abandoned, which is a division of application No. 08/801,036, filed on Feb. 19, 1997, now Pat. No. 5,840,081, which is a continuation of application No. 08/569,314, filed on Dec. 8, 1995, now abandoned, which is a continuation of application No. 08/352,127, filed on Dec. 1, 1994, now abandoned, which is a division of application No. 08/261,235, filed on Jun. 14, 1994, now Pat. No. 5,411,552, which is a continuation of application No. 07/961,891, filed as application No. PCT/DK91/00134 on May 16, 1991, now abandoned.

(30) Foreign Application Priority Data

May 18, 1990 (DK) .................................... 1246/90

(51) Int. Cl.
*A61F 2/24* (2006.01)
*A61F 2/90* (2006.01)
*A61F 2/88* (2006.01)

(52) U.S. Cl. ..................... 623/1.26; 623/2.14
(58) Field of Classification Search ......... 623/2.1–2.19, 623/2.38–2.41, 900, 904, 1.24–1.26, FOR. 101, 623/23.68; 604/9
See application file for complete search history.

(56) References Cited

U.S. PATENT DOCUMENTS 2,055,188 A  9/1936  Wappler et al.

(Continued)

FOREIGN PATENT DOCUMENTS

DE  2246526  3/1973

(Continued)

OTHER PUBLICATIONS

Sugie et al., Clinical experience with supported homograft heart valve for mitral and aortic valve replacement, The Journal of Thoracic and Cardiovascular Surgery, vol. 57, No. 4 (Apr. 1969), pp. 455-463.*

(Continued)

*Primary Examiner*—David H. Willse
(74) *Attorney, Agent, or Firm*—David L. Hauser

(57) ABSTRACT

A valve prosthesis for implantation in the body by use of a catheter includes a stent made from an expandable cylinder-shaped thread structure including several spaced apices. The elastically collapsible valve is mounted on the stent as the commissural points of the valve are secured to the projecting apices. The valve prosthesis can be compressed around balloons of the balloon catheter and inserted in a channel, for instance, in the aorta. When the valve prosthesis is placed correctly, the balloons are inflated to expand the stent and wedge it against the wall of the aorta. The balloons are provided with beads to ensure a steady fastening of the valve prosthesis on the balloons during insertion and expansion. The valve prosthesis and the balloon catheter make it possible to insert a cardiac valve prosthesis without a surgical operation involving opening the thoracic cavity.

49 Claims, 5 Drawing Sheets

U.S. PATENT DOCUMENTS

| | | |
|---|---|---|
| 3,275,211 A | 9/1966 | Hirsch et al. |
| 3,409,013 A | 11/1968 | Berry |
| 3,472,230 A | 10/1969 | Fogarty |
| 3,548,417 A | 12/1970 | Kischer |
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancodk |
| 3,799,150 A | 3/1974 | Bonnet |
| 3,868,956 A | 3/1975 | Alfidi et al. |
| 4,035,849 A | 7/1977 | Angell et al. |
| 4,038,703 A | 8/1977 | Bokros |
| 4,056,854 A | 11/1977 | Boretos et al. |
| 4,106,129 A | 8/1978 | Carpentier et al. |
| 4,222,126 A | 9/1980 | Boretos et al. |
| 4,297,749 A | 11/1981 | Davis et al. |
| 4,339,831 A | 7/1982 | Johnson |
| 4,343,048 A * | 8/1982 | Ross et al. ............... 623/2.14 |
| 4,345,340 A | 8/1982 | Rosen |
| 4,391,282 A | 7/1983 | Amdo et al. |
| 4,448,195 A | 5/1984 | LeVeen et al. |
| 4,470,157 A | 9/1984 | Love |
| 4,574,803 A | 3/1986 | Storz |
| 4,580,568 A | 4/1986 | Gianturco |
| 4,592,340 A | 6/1986 | Boyles |
| 4,612,011 A | 9/1986 | Kautzky |
| 4,655,771 A | 4/1987 | Wallsten |
| 4,687,483 A * | 8/1987 | Fisher et al. ............... 623/2.14 |
| 4,692,164 A | 9/1987 | Dzemeshkevich et al. |
| 4,725,274 A | 2/1988 | Lane et al. |
| 4,731,074 A | 3/1988 | Rousseau et al. |
| 4,733,665 A | 3/1988 | Palmaz |
| 4,777,951 A | 10/1988 | Cribier et al. |
| 4,778,461 A | 10/1988 | Pietsch et al. |
| 4,787,899 A | 11/1988 | Lazarus |
| 4,787,901 A | 11/1988 | Baykut |
| 4,790,843 A | 12/1988 | Carpentier et al. |
| 4,796,629 A | 1/1989 | Grayzel |
| 4,830,003 A | 5/1989 | Wolff et al. |
| 4,851,000 A | 7/1989 | Gupta |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,892,541 A | 1/1990 | Alonso |
| 4,917,698 A | 4/1990 | Carpentier et al. |
| 4,922,905 A | 5/1990 | Strecker |
| 4,932,965 A | 6/1990 | Phillips |
| RE33,258 E | 7/1990 | Onik |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,007,896 A | 4/1991 | Shiber |
| 5,019,102 A | 5/1991 | Hoene |
| 5,026,366 A | 6/1991 | Leckrone |
| 5,032,128 A | 7/1991 | Alonso |
| 5,037,434 A | 8/1991 | Lane |
| 5,041,130 A | 8/1991 | Cosgrove et al. |
| 5,047,041 A | 9/1991 | Samuels |
| 5,059,177 A | 10/1991 | Towne et al. |
| 5,061,277 A | 10/1991 | Carpentier et al. |
| 5,085,635 A | 2/1992 | Cragg |
| 5,089,015 A | 2/1992 | Ross |
| 5,104,407 A | 4/1992 | Lam et al. |
| 5,123,919 A | 6/1992 | Sauter et al. |
| 5,147,391 A | 9/1992 | Lane |
| 5,152,771 A | 10/1992 | Sabbaghian et al. |
| 5,163,953 A | 11/1992 | Vince |
| 5,163,955 A | 11/1992 | Love et al. |
| 5,167,628 A | 12/1992 | Boyles |
| 5,201,880 A | 4/1993 | Wright et al. |
| 5,258,021 A | 11/1993 | Duran |
| 5,258,023 A | 11/1993 | Reger |
| 5,295,958 A | 3/1994 | Shturman |
| 5,306,296 A | 4/1994 | Wright et al. |
| 5,332,402 A | 7/1994 | Teitelbaum |
| 5,332,403 A | 7/1994 | Kolff |
| 5,344,442 A | 9/1994 | Deac |
| 5,350,420 A | 9/1994 | Cosgrove et al. |
| 5,358,518 A | 10/1994 | Camilli |
| 5,370,685 A | 12/1994 | Stevens |
| 5,376,112 A | 12/1994 | Duran |
| 5,376,113 A | 12/1994 | Jansen et al. |
| 5,397,351 A | 3/1995 | Pavcnik et al. |
| 5,411,552 A | 5/1995 | Andersen et al. |
| 5,443,446 A | 8/1995 | Shturman |
| 5,449,384 A | 9/1995 | Johnson |
| 5,469,868 A | 11/1995 | Reger |
| 5,480,424 A | 1/1996 | Cox |
| 5,489,298 A | 2/1996 | Love et al. |
| 5,500,014 A | 3/1996 | Quijano et al. |
| 5,545,209 A | 8/1996 | Roberts et al. |
| 5,554,185 A | 9/1996 | Block et al. |
| 5,609,626 A | 3/1997 | Quijano et al. |
| 5,755,782 A | 5/1998 | Love et al. |
| 5,824,061 A | 10/1998 | Quijano et al. |
| 5,840,081 A | 11/1998 | Andersen et al. |
| 6,283,993 B1 | 9/2001 | Cosgrove et al. |

FOREIGN PATENT DOCUMENTS

| | | | |
|---|---|---|---|
| DE | 36 40 745 A1 | 6/1987 | |
| EP | 0103546 A1 | 3/1984 | |
| EP | 0350302 | 1/1990 | |
| EP | 0357003 | 3/1990 | |
| EP | 0592410 B1 | 10/1995 | |
| GB | 1 268 484 * | 3/1972 | |
| GB | 2 056 023 A | 3/1979 | |
| GB | 2056023 | 3/1981 | |
| SU | 158988 * | 11/1963 | ........ 623/FOR. 101 |
| SU | 1258406 | 9/1986 | |
| SU | 1271508 | 11/1986 | |
| SU | 1271508 A1 | 11/1986 | |
| SU | 1371700 A1 * | 2/1988 | |
| SU | 1371701 | 2/1988 | |
| SU | 1457921 A1 * | 2/1989 | |
| WO | WO 9117720 | 11/1991 | |
| WO | WO 9217118 | 10/1992 | |

OTHER PUBLICATIONS

Anderson, et al., "Transluminal implantation of artificial heart valves. Description of a new expandable aortic valve and initial results with implantation by catheter technique in closed chest pigs", European Heart Journal, the journal of the European Society of Cardiology, vol. 13, Issue 5, pp. 704-708, (1992).

LexisNexis Search Results, U.S. District Court Civil Docket, U.S. District—Delaware (Wilmington), Civil Action No. 1:08-cv-00091-GMS, *Edwards Lifesciences AG et al v. Corevalve Inc.*, filed Feb. 12, 2008, Date of last filing Apr. 4, 2008, 7 sheets.

Morris, Nichols, Arsht & Tunnell LLP, Attorneys for Plaintiffs, Demand for Jury Trial filed Feb. 12, 2008 in the United States District Court for the District of Delaware, Case 1:08-cv-00091-UNA, Document 1, 41 sheets.

Richards, Layton & Finger, Attorneys for Defendant, CoreValve, Inc., Jury Trial Demanded filed Apr. 4, 2008 in the United States District Court for the District of Delaware, Case 1:08-cv-00091-GMS, Document 12, 13 pages.

H.R. Andersen et al., Transluminal implantation of artificial heart valves. Description of a new expandable aortic valve and initial results with implantation by catheter technique in closed chest pigs, European Heart Journal (1992) 13, 704-708.

Ernst-Peter Strecker, M.D., et al., Current Status of the Stecker Stent, Contemporary Interventional Techniques, Supplied by The British Library—"The world's knowledge", vol. 12, No. 1, Nov. 1994, pp. 673-687.

Steven R. Bailey, 75—Percutaneous Expandable Prosthetic Valves, Textbook of Interventional Cardiology, vol. 2, Second Edition, 1994, pp. 1268-1276.

*Corevalve, Inc.* v. *Edwards Lifesciences AG and Edwards Lifesciences PVT, Inc.*, High Court of Justice—Chancery Division Patents Court, United Kingdom, Case No. HC-07-C01243, Amended Product Description of Claimant, 7 pgs.

Dotter, Charles T., MD, Transluminally-placed Coilspring Endarterial Tube Grafts: Long-term Patency in Canine Popliteal Artery, Investigate Radiology, Sep.-Oct. 1969, pp. 329-332, vol. 4, Issue 5, Lippincott Wiiliams & Wilkins, Inc.

*Edwards Lifesciences AG and Edwards Lifesciences LLC* v. *Corevalve, Inc.*, United States District Court for the District of Delaware, Civil Action No, 1:08-CV-00091-GMS, Edwards' Opening Claim Construction Brief, Feb. 6, 2009 26 pgs.

*Edwards Lifesciences AG and Edwards Lifesciences LLC* v. *Corevalve, Inc.*, United States District Court for the District of Delaware, Civil Action No. 1:08-CV-00091-GMS, Joint Markman Claim Construction Chart, Jan. 16, 2009, 32 pgs.

*Edwards Lifesciences AG and Edwards Lifesciences LLC* v. *Corevalve, Inc.*, United States District Court for the District of Delaware, Civil Action No. 1:08-CV-00091-GMS, Joint Supplemental Markman Claim Construction Chart, 4 pgs.

*Edwards Lifesciences AG and Edwards Lifesciences LLC* v. *Corevalve, Inc.*, United States District Court for the District of Delaware, Civil Action No. 1:08-CV-00091-GMS, Order Construing the Terms of U.S. Patent Nos. 5,411,552; 6,168,614; and 6,582,462, 5 pgs.

Request for Ex Parte Reexamination filed Jun. 12, 2009 for USPN 5,411,552, Issued May 2, 1995, Titled: Valve Prothesis for Implantation in the Body and a Catheter for Implanting Such Valve Prothesis.

Davies, Hywel, "Catheter-Mounted Valve for Temporary Relief of Aortic Insufficiency"; The Lancet, Preliminary Communications; Jan. 30, 1965, p. 250, Cardiac Department, Guy's Hospital, London, S.E.1.

Dotter, M.D., Charles T., "Transluminally-placed Coilspring Endarterial Tube Grafts"; Investigative Radiology, Sep.-Oct., 1969, vol. 4, pp. 329-332.

Magovern, George J., Replacement of Aortic and Mitral Valves with the Sutureless Prosthesis; Results in 100 Patients; Chest Online; American College of Chest Physicians; ISSN: 0096-0217; wvvvv.chestjournal.org; pp. 415-422, Dis Chest 1966; 50; 415-422.

Decision on Request for Reexamination in U.S. Appl. No. 09/009,484, filed Jun. 12, 2009; mailed Aug. 7, 2009.

Andersen, Henning Rud, History of Percutaneous Aortic Valve Prosthesis, Herz 34 2009 Nr.5 Urban & Vogel, pp. 343, 346, Skejby University Hospital Department of Cardiology, Aarhus, Denmark.

16th Ediiton of The Merck Manual of Diagnosis and Therapy (1992) "Valvular Heart Disease," pp. 546-553.

Yamaguchi, Case Description "A Case of a Reoperation Using a Balloon Catheter with Blocked Pars Ascendes Aortae" Kyobu Geka, Oct. 1989, 42:11, pp. 961-964.

World Medical Manufacturing Corp., Talent Endovascular Bifurcated Spring Graft System Composite Design brochure, c. 1989.

Derwent Abstract No. 87-1980867/27 (1987), SU 1271508 (Gorkii Kirov Medical Ins.).

UK proceedings in respect of EP 0592410, May 21, 2007.

\* cited by examiner

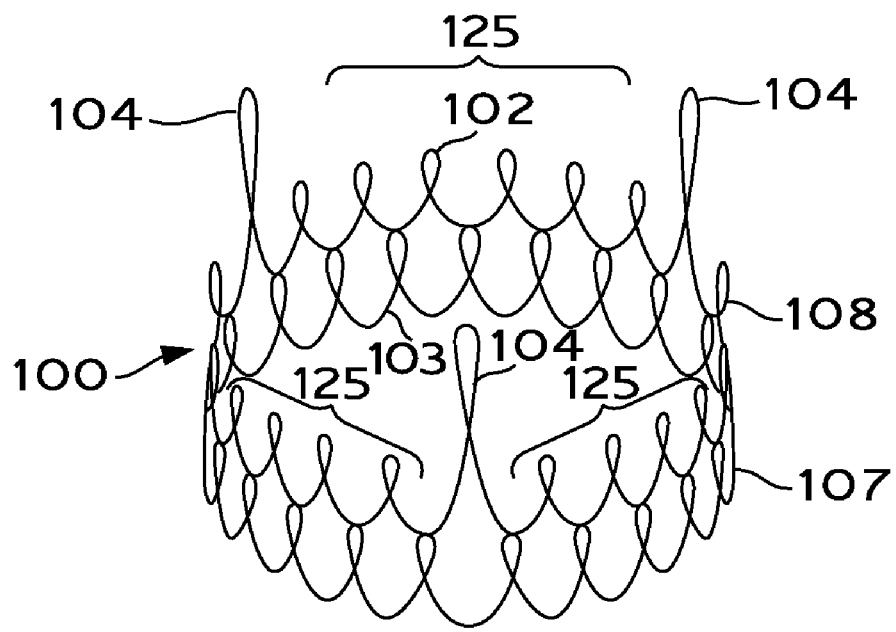
F I G. 13
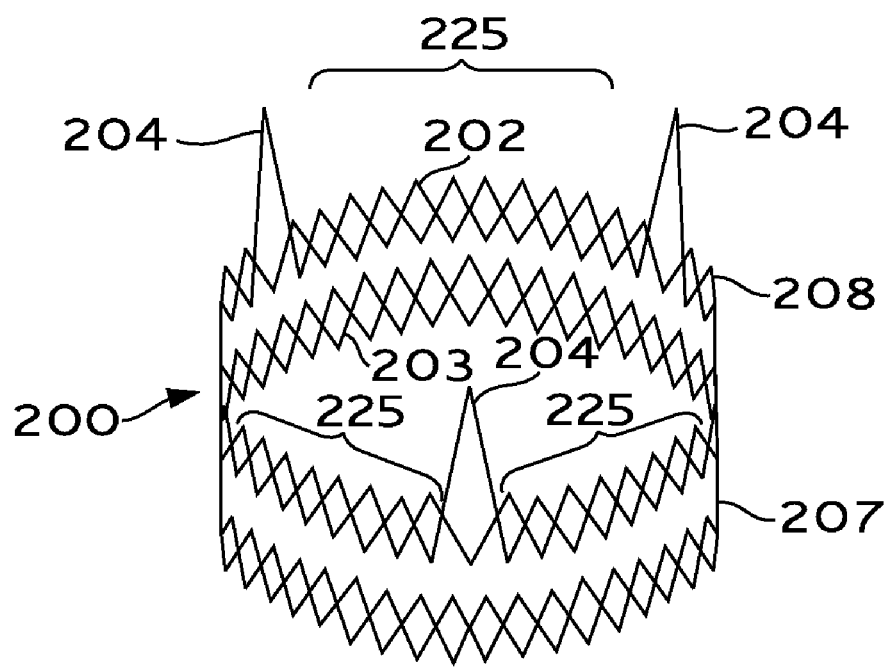
F I G. 14

VALVE PROSTHESIS FOR IMPLANTATION IN THE BODY AND A CATHETER FOR IMPLANTING SUCH VALVE PROSTHESIS

CROSS REFERENCE TO RELATED APPLICATION

This application is a continuation of U.S. patent application Ser. No. 09/514,426, filed Feb. 28, 2000, (now U.S. Pat. No. 6,582,462), which is a continuation of U.S. patent application Ser. No. 09/026,574, filed Feb. 20, 1998 (now U.S. Pat. No. 6,168,614), which is a continuation of U.S. patent application Ser. No. 08/955,228, filed Oct. 21, 1997 (abandoned), which is a divisional of U.S. patent application Ser. No. 08/801,036, filed Feb. 19, 1997 (issued as U.S. Pat. No. 5,840,081 on Nov. 24, 1998), which is a continuation of U.S. patent application Ser. No. 08/569,314, filed Dec. 8, 1995 (abandoned), which is a continuation of U.S. patent application Ser. No. 08/352,127, filed Dec. 1, 1994 (abandoned), which is a divisional of U.S. patent application Ser. No. 08/261,235, filed Jun. 14, 1994 (now U.S. Pat. No. 5,411,552), which is a continuation of U.S. patent application Ser. No. 07/961,891, filed Jan. 11, 1993 (abandoned), which is a national stage application of PCT/DK91/00134, filed May 16, 1991 (abandoned).

BACKGROUND OF THE INVENTION

The present invention relates to a valve prosthesis, preferably a cardiac valve prosthesis, for implantation in the body and comprising a collapsible elastic valve which is mounted on an elastic stent wherein the commissural points of the elastic collapsible valve are mounted on the cylinder surface of the elastic stent.

Valve prostheses of this type are usually implanted in one of the channels of the body to replace a natural valve. In the present description the invention will be explained in connection with a cardiac valve prosthesis for implantation in aorta. However, it will be possible to use a valve prosthesis according to the invention in connection with implantation in other channels in the body by using the same technique as the one used for implantation of cardiac valve prosthesis. Such an implantation may, e.g., comprise the implantation of:
1. a valve (for instance a cardiac valve) in the veins,
2. a valve in the esophagus and at the stomach,
3. a valve in the ureter and/or the vesica,
4. a valve in the biliary passages,
5. a valve in the lymphatic system, and
6. a valve in the intestines.

An existing natural valve in the body is traditionally replaced with a valve prosthesis by a surgical implantation. However, a surgical implantation is often an exacting operation. Thus, today the implantation of cardiac valves are solely made by surgical technique where the thoracic cavity is opened. The operation calls for the use of a heart and lung machine for external circulation of the blood as the heart is stopped and opened during the surgical intervention and the artificial cardiac valves are subsequently sewed in.

Due to its exacting character, it is impossible to offer such operation to certain people. For instance, this is due to the fact that the person is physically weak because of age or illness. Moreover, the number of heart and lung machines available at a hospital will be a substantially limiting factor.

Cardiac valve prostheses that need no surgical intervention are known as there are used for implantation by means of a technique of catheterization. Examples of such valve prostheses are described in U.S. Pat. Nos. 3,671,979 and 4,056,854. However, both of these valve prostheses are connected to means which lead to the surface of the patient either for a subsequent activation of the valve or for a subsequent reposition or removal of the valve prosthesis. With these valve prostheses it is impossible to make an implantation which makes it possible for the patient to resume a substantially normal life in the same way as it is possible in connection with a surgical implantation of a cardiac valve.

From U.S. Pat. No. 3,755,823 an elastic stent for a cardiac valve prosthesis is known. However, this valve prostheses is not designed for implantation in the body by catheterization. Even though this patent contains no detailed explanation, the description indicates that this valve prosthesis is designed for implantation and sewing on by a surgical intervention.

Moreover, from U.S. Pat. Nos. 4,856,516 and 4,733,665 different shapes of expandable stents are known. These stents are made to be expanded by impression of a radially outward force coming from a balloon catheter or the like. These stents are made to reinforce the wall when there is a risk that the channel is closed and/or compressed.

The nearest prior art may be that the described in GB-A-2,056,023. This document discloses an elastic stent as described by way of introduction. Thus, the stent described comprises an elastic collapsible valve mounted on the cylinder surface of a cylindrical stent. However, the valve prosthesis including the stent is designated for mounting through a surgical intervention. Even though the stent is slightly collapsible, it will not be suited for implantation by a catheterization procedure.

SUMMARY OF THE INVENTION

It is the object of the present invention to provide a valve prosthesis of the type mentioned in the introductory part, which permits implantation without surgical intervention in the body and by using a catheter technique known per se and which makes it possible for the patient to resume a substantially normal life.

This is achieved according to the invention with a valve prosthesis of the type mentioned in the introductory part, which is characterized in that the stent is made from a radially collapsible and re-expandable cylindrical support means for folding and expanding together with the collapsible valve for implantation in the body by means of a technique of catheterization.

The collapsible elastic valve is mounted on the stent for instance by gluing, welding or by means of a number of suitable sutures.

If the support means are made from a thread structure, this can for instance be grate shaped, loop shaped or helical. This makes it possible to compress the stent and the collapsible valve mounted thereon for placing on the insertion catheter. The use of a non-self-expandable stent may, e.g., be effected by a compression of the stent around the expansion arrangement of the catheter which preferably consists of a balloon. When using a self-expandable stent, a catheter with an expansion arrangement is not used. In this case the stent is compressed and is inserted into an insertion or protection cap from which the stent is eliminated after implantation in order to obtain an expansion due to the stresses in the compressed support means, which for instance may be made from plastics or metal. After the compression the entire outer dimension is relatively small, which makes it possible to introduce the valve prostheses through a channel in the body.

When the valve prosthesis is introduced and placed correctly, the stent is expanded by self-expansion or by means of the expansion arrangement until the stent is given an outer dimension which is slightly larger than the channel in which it is placed. As the stent is elastic, a contraction of the stent is prevented once it is expanded. The stiffness in the material of the support means contributes to maintain the expanded shape of the stent. After the expansion is made, the expansion arrangement of the catheter is contracted and the catheter can be removed from the channel. The inlet opening can subsequently be closed and the patient will then be able to resume a normal life.

The valve prosthesis according to the invention does not require an actual operation but merely a small intervention to optionally expose the body channel, e.g., a vein, through which the insertion takes place. Thus, patients for whom an operation would be associated with high risk can be offered implantation of, for instance, cardiac valves. After the implantation has taken place, the after-treatment will advantageously be shorter than normal, which means fewer hospital days for the patient. Moreover, it is assumed that it will be possible to implant the valve prosthesis under local anaesthetic.

The valve prosthesis can be used to replace a natural valve or to establish a new valve function in one of the channels in the body which do not naturally contain a valve. For instance this goes for veins (arteries and veins) on a place without natural valves. The function of the valve prosthesis is then to ensure that the blood flows in one direction only. The valve is meant to be used in veins in the legs of persons suffering from varicose veins (varices).

In persons having varicose veins the blood flows in a wrong direction, viz. from the central veins in the center of the leg towards the superficial veins. Among other things, this is due to the changed pressure in the legs, upright working position and other conditions. A valve prosthesis according to the invention may easily be placed in the veins and prevent the flow of the blood in a wrong direction.

Also, the valve prosthesis can be used in connection with diseases, for instance cancerous tumors, where too much humour is produced. If the humour is able to flow from the cancerous tumor through several channels, it is possible to drain the humour in one desired direction through the channels of the body by an appropriate placing of the valve prosthesis.

When the valve prosthesis is used as a cardiac valve prosthesis in the aorta, it is possible to mount it in three positions, viz., in the descending part of the aorta in a position between the coronary arteries and the left ventricle of the heart, or in the aorta in a position immediately after the mouth of the coronary arteries.

The cardiac valve prosthesis can also be used in other places than in the aorta. Thus, the valve prosthesis can be used in the pulmonary artery and/or the right ventricle of the heart for replacing the pulmonary valves. Likewise, the cardiac valve prosthesis can be used in the passage between the right auricle of the heart and the right ventricle of the heart (tricuspidalostium) and the passage between the left auricle of the heart and the left ventricle of the heart (mistralostium) for replacing the tricuspidal valve and the mitral valve, respectively.

Even though the cardiac valve preferably is meant to be used for patients suffering from aorta insufficiency and who cannot be offered an open heart surgery, the valve prosthesis can also be used for patents in connection with treatment of aorta stenosis. Several of the patients with aorta stenosis are elderly people who cannot be offered a surgical cardiac operation. The patients are offered balloon dilatation of the aorta stenosis which may result in an aorta insufficiency as a side effect of the treatment.

As to these patients it is possible to insert a valve prosthesis in the descending or ascending part of the aorta thoracalis a few days or weeks before the balloon dilatation. As a result thereof, the left ventricle is protected against weight if the subsequent balloon dilatation of the stenosis results in aorta insufficiency. In certain cases the weight (reflux) on the left ventricle is reduced by up to approximately 75%.

Furthermore, the stent may be made with a relatively great height and with a cylinder surface which is closed by a suitable material. Thus, a vascular prosthesis known per se is formed wherein the valve is mounted. This may facilitate the implantation of the valve prosthesis, for instance in the arcus aorta. Moreover, the great surface which abuts the inner wall of the channel contributes to ensure the securing of the valve prosthesis in the channel. This embodiment is also suitable as valve prosthesis which is inserted in veins. As veins have relatively thin and weaker walls than arteries, it is desirable that the valve prosthesis has a greater surface to distribute the outward pressure which is necessary to secure the valve prosthesis.

Moreover, the invention relates to a balloon catheter for implanting a valve prosthesis according to the invention and comprising a channel for injection of a fluid for the inflation of the balloon means of the catheter and an insertion cap wherein the balloon means of the catheter and a collapsible valve prosthesis mounted thereon are located during the injection, characterized in that the balloon means are provided with profiled surface which is made to ensure a steady fastening of the valve prosthesis during the withdrawal of the balloon means from the protection cap and the subsequent inflation for the expansion of the stent.

Different balloon catheters for implanting cores in the body are known. For instance, such balloon catheters are known from U.S. Pat. Nos. 4,856,516, 4,733,665 and 4,796,629 and from DE publication No. 2,246,526. However, the known balloon catheters have a smooth or a slightly wavy surface. The use of such balloon catheter is disadvantageous for mounting a valve prosthesis in a channel having a large flow as for instance the aorta. A large humour flow is able to displace the stent on the smooth surface of the balloon and makes an accurate positioning difficult. This drawback has been remedied with the balloon catheter according to the present invention as the profiled surface prevents a displacement of the valve prosthesis in relation to the balloon means during introduction and the subsequent inflation of the balloon means.

In connection with the implantation, any prior art technique may be used to supervise an accurate introduction and positioning of the valve prosthesis. Thus, guide wires for the catheter, X-ray supervision, injection of X-ray traceable liquids, ultrasonic measuring, etc. may be used.

DESCRIPTION OF THE DRAWINGS

The invention will now be explained in detail with reference to the accompanying schematical drawing, wherein FIGS. 13-14 are perspective views illustrating two further embodiments of a stent without a valve.

DETAILED DESCRIPTION OF THE PREFERRED EMBODIMENTS

Figure 1:
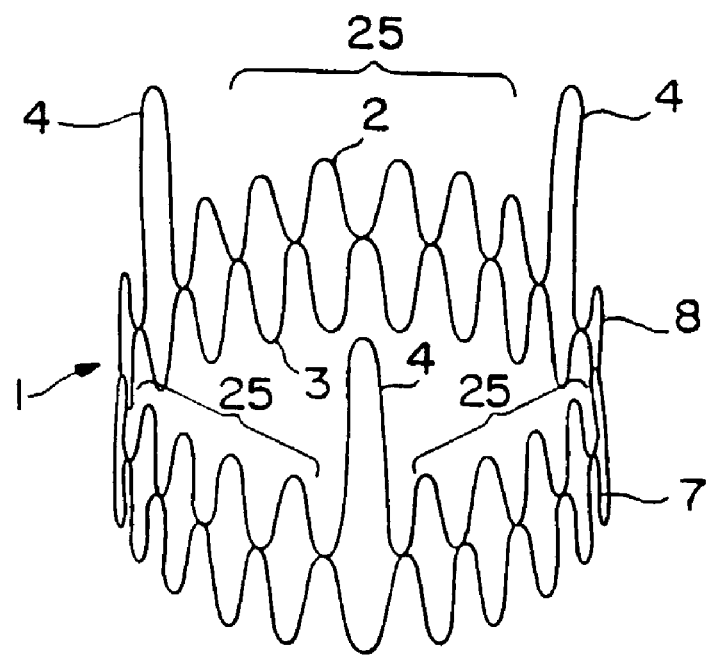
FIG. 1 shows a perspective view of a stent without a valve.
Figure 2:
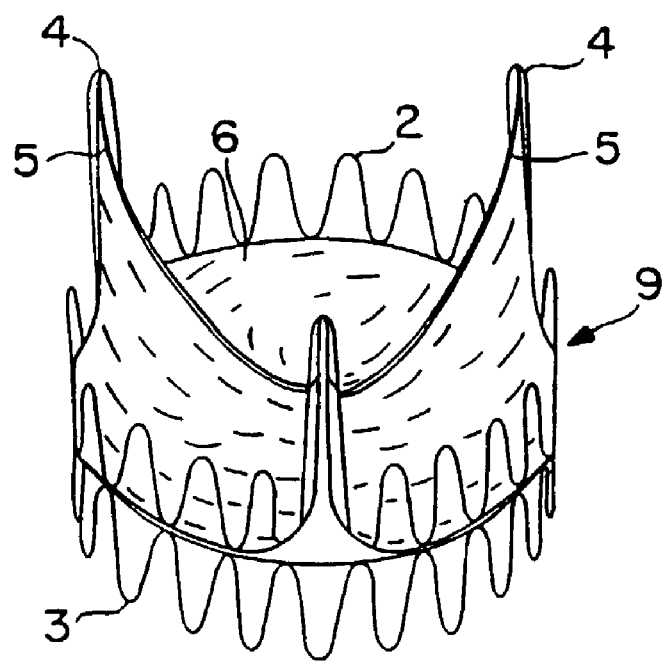
FIG. 2 is a perspective view of a valve prosthesis according to the invention made from the stent shown in FIG. 1 having a biological valve mounted thereon.

FIG. 1 shows a stent 1 made by support means in the form of two 0.55 mm surgical stainless steel wires 2,3. The wires are folded in 15 loops. Three loops 4 are 14 mm in height and are intended to secure the commissural points 5 (see FIG. 2) from a biological cardiac valve 6 which is mounted in the stent 1. The remaining loops have a height of 8 mm. These loops form circumferentially expandable sections 25 between the commissural points 5 forming commissural supports. Each of the two folded wires 2,3 is bent to form rings 7,8 which are closed by welding the ends. The two rings are placed on top of each other as will appear from FIG. 1 and they are mutually secured by means of a number of sutures (not shown). The lower ring is circumferentially expandable at least along sections thereof which correspond to the circumferentially expandable sections 25. By using a substantially cylindrical thread structure with projecting apices, a reduction in weight is obtained as compared to a stent which is exclusively cylindrical with the same loop heights for all the loops.

The biological valve 6 was removed from a slaughtered pig of 100 kg. The valve was cleaned before mounting in the stent 1. The cleaned valve has an outer diameter of 25-27 mm and the height of the three commissural points 5 is 8 mm. The valve 6 is mounted in the stent by means of a suitable number of sutures to form the cardiac valve prosthesis 9 shown in FIG. 2. The valve prosthesis produced is used for performing tests in pigs by implantation of cardiac valve prosthesis. However, the cardiac valve prosthesis for use in human beings has a corresponding form.

Figure 3:
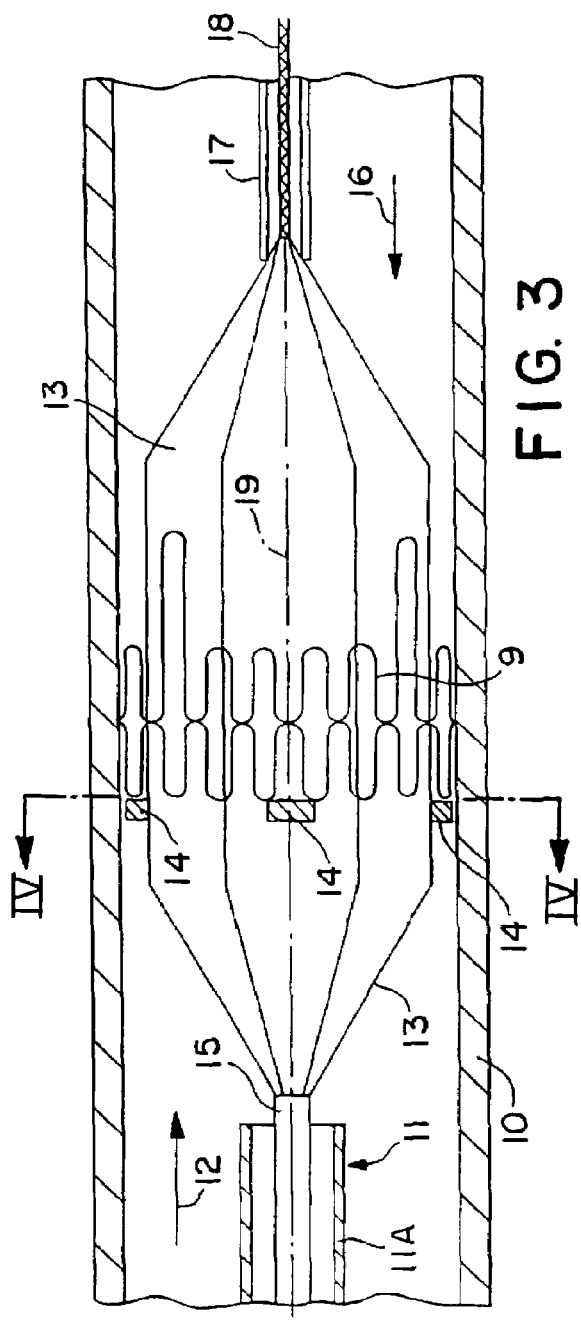
FIG. 3 is a partial view through the aorta illustrating a partially inflated balloon catheter.

FIG. 3 shows a partial view through the aorta 10. A balloon catheter 11 is introduced in the aorta according to the direction of an arrow 12. In the Figure shown the balloon means 13 of the balloon catheter is led out of the protection cap 11A and is partly inflated through a fluid channel 15, which is led to the surface of the patient. The balloon means 13 constitutes a tri-sectional balloon upon which the cardiac valve prosthesis is placed. In the form shown, the cardiac valve prosthesis is expanded exactly to be in contact with the aorta 10. The balloon means 13 is provided with three projecting beads 14 which are engaged with the one side of the cardiac valve prosthesis 9. The blood flowing through the aorta according to the direction of an arrow 16 will thus cause the cardiac valve prosthesis 9 to abut on the beads 14 and the valve cannot be displaced in relation to the balloon means 13. Moreover, the balloon catheter used comprises a central channel 17 to receive a guide wire 18 which is used in a way known per se for supervising the introduction of the catheter through fluoroscopi. In the shown embodiment beads 14 are only used at one side of the valve prosthesis, but, however, it will often be desirable to use the beads in pairs placed along lines parallel to the longitudinal axes 19 through the balloon means 13. In this case the spacing of the pair of beads 14 will correspond to the height of the loops of the stent. This makes it possible to make an effective fastening of a valve prosthesis on balloon means. Moreover, the fastening on the balloon means may be provided by using balloon means with an indentation in the surface (not shown).

Figure 4:
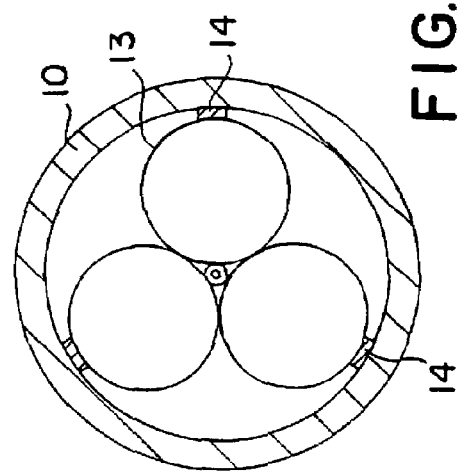
FIG. 4 is a cross section through the embodiment shown in FIG. 9, FIGS. 5-7 are views illustrating the introduction and implantation of a valve prosthesis of the invention in the aorta.

FIG. 4 shows a cross section through the embodiment shown in FIG. 3 illustrating the placing of the beads 14 on the tri-sectional balloon means 13.

A balloon catheter of the above-described type which was used in tests of implanting of cardiac valve prosthesis 9 in pigs had the following dimensions. Each of the three balloons was 60 mm in length and 15 mm in diameter. The total diameter for the three inflated balloons was 31 mm and in the balloon catheter used two beads 14 having a height of 3 mm were mounted on each side of the three balloons. The beads had a spacing of 15 mm. The protection cap 11A of the balloon catheter had an outer diameter of 13.6 mm and an inner diameter of 12.5 mm and a length of 75 cm. The balloon catheter was provided with a standard guide wire having a diameter of 0.9 mm and a length 300 cm.

Figure 5:
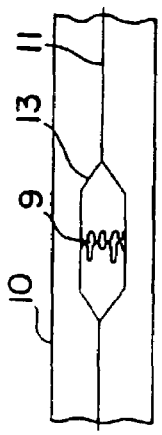
Figure 6:
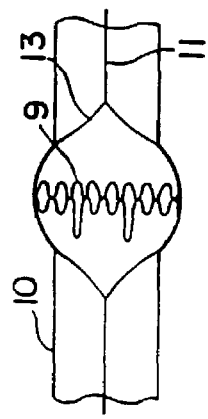
Figure 7:
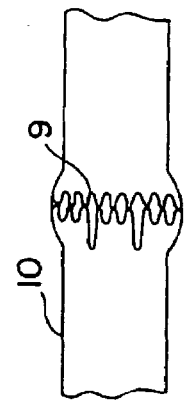

FIGS. 5-7 show the valve prosthesis 9 at different steps in introducing and implanting in the aorta 10 by means of the catheter 11 having the inflatable balloon means 13. The cardiac valve prosthesis 9 is initially placed above the deflated balloon means 13 and compressed manually around the balloon means (FIG. 5), whereafter the outer diameter for the valve prosthesis is approximately 10 mm. After the introduction and positioning, the balloon means 13 is inflated (FIG. 6), thereby contributing an outer dimension of approximately 30 mm to the cardiac valve prosthesis. To obtain an effective fastening in the aorta, the outer dimension of the cardiac valve prosthesis is greater than the diameter of the aorta. This means that the prosthesis is tight against the inner wall of the aorta with a pressure which is sufficiently large to counteract a detachment due to the flow of the blood. The balloon catheter 11 may subsequently be removed from the aorta 10 (FIG. 7). Due to the stiffness of the metal the valve prosthesis will prevent a contraction. However, smaller contractions may occur (<10% diameter reduction) after the deflation and removal of the balloon catheter 13. When the valve prosthesis is mounted as shown in FIG. 7, the patient will be able to resume a substantially normal life after a few days.

Figure 8:
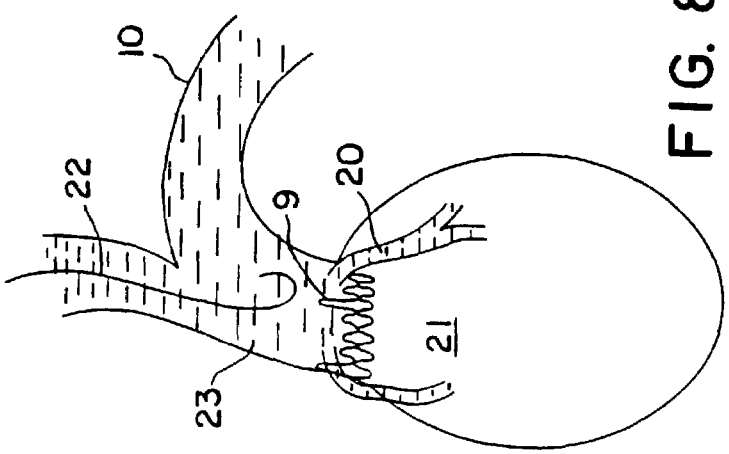
FIGS. 8-10 are views illustrating three possible positions of a cardiac valve prosthesis.
Figure 9:
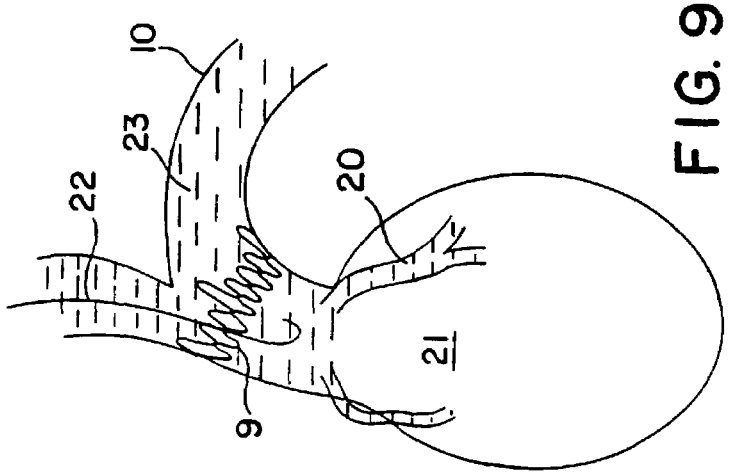
Figure 10:
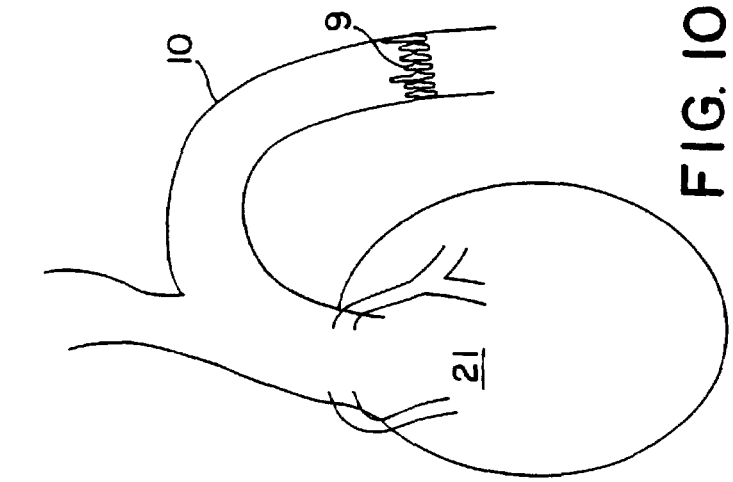

FIGS. 8-10 show the positioning of the valve prosthesis 9 as cardiac valve prosthesis in the aorta 10 in three different positions, i.e., in a position between the coronary arteries 20 and the left ventricle of the heart 21 (FIG. 8), in a position immediately after the mouth of the coronary arteries in the ascending part of the aorta (FIG. 9), and in a position in the descending part of the aorta 10. The positioning of the valve prosthesis is chosen in accordance with the diagnosis of the illness of the patient. By placing the cardiac valve prosthesis as shown in FIG. 8, there is a risk of detachment and/or covering the mouth of the coronary arteries, and therefore it is preferred to use a higher stent which, for instance, comprises several ranges placed on top of each other. This allows a fixation of the prosthesis at a place after the mouth of coronary arteries even though the valve itself is in the position between the coronary arteries and the left ventricle. FIGS. 8 and 9 show how a contrast medium 23 is injected by means of a so-called pigtail catheter for registration of tightness of the implanted valve prosthesis 9.

A specific embodiment for a valve prosthesis and a balloon catheter for implanting the valve prosthesis has been explained above. However, it is obvious that it is possible to modify the valve prosthesis depending on the desired use, and moreover, it is possible to modify the catheter used in the implantation. Thus, the stent of the valve prosthesis may be made solely of one closed ring folded in a number of loops or with three or more mutually secured loop-shaped rings placed on top of each other. Moreover, it is possible to make the stent having a thread structure which instead of loops is grate shaped, helical or is formed otherwise if only it is ensured that the form of the stent permits the compression and expansion of the stent and fastening of the collapsible valve. Instead of a biological valve it might be possible to use other collapsible valves, such as valves made from synthetic materials, e.g., polyurethane. It is also possible to use valves with more or fewer flaps than three.

Figure 11:
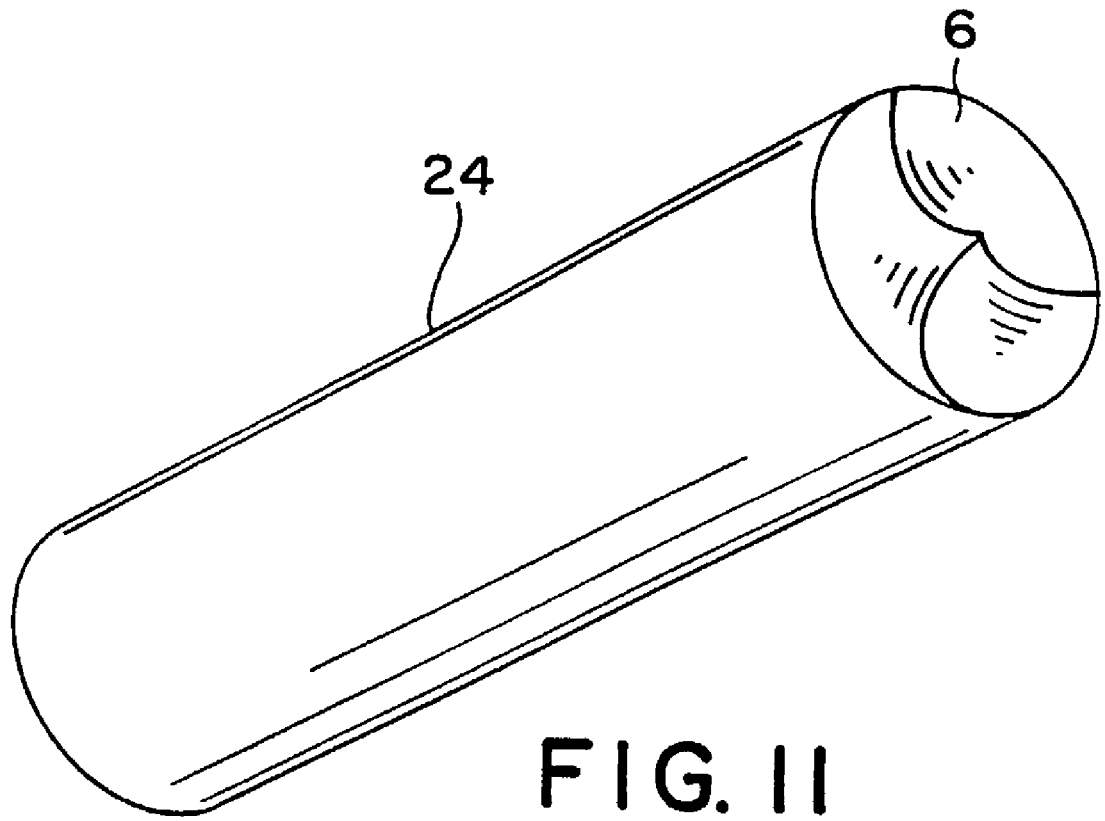
FIGS. 11-12 are perspective views illustrating two further embodiments of a valve prosthesis having a closed cylindrical wall.
Figure 12:
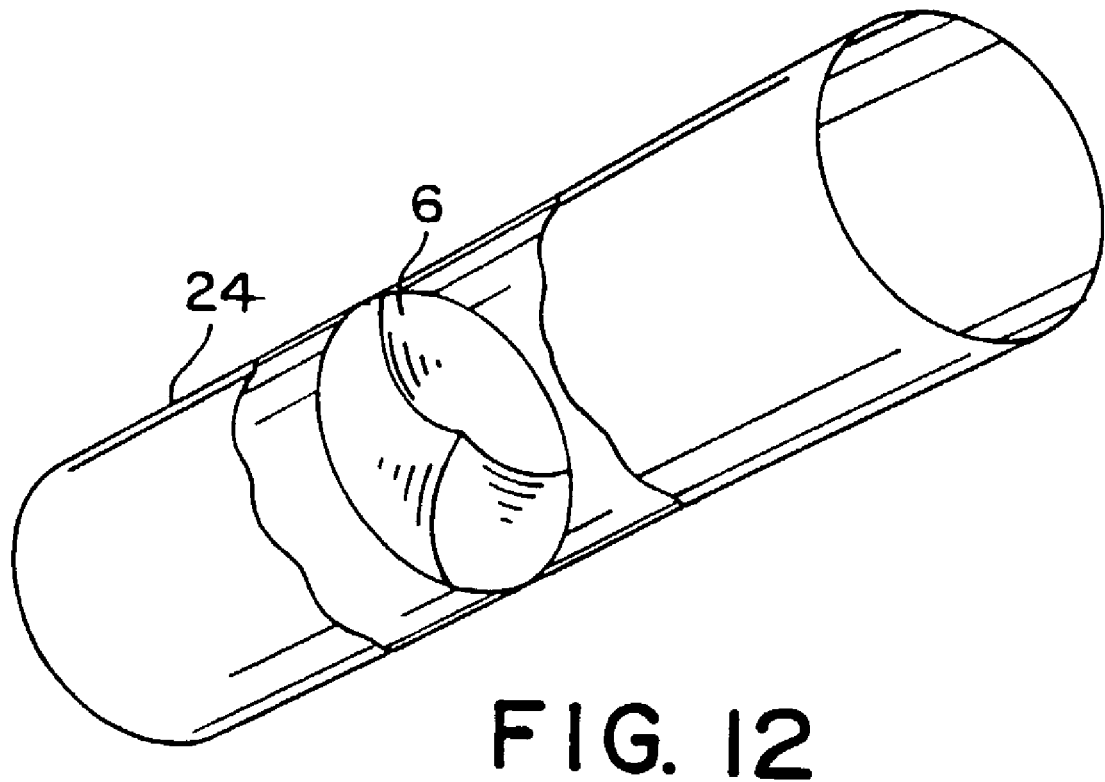

It is possible to make the valve prosthesis with a closed cylinder surface as illustrated in FIGS. 11 and 12. In both Figures the support means of the valve prosthesis is made of an elongated tubular means 24 having a closed cylinder surface. This valve prosthesis is intended to expand by self-expansion or by means of a catheter according to the invention. This prosthesis is especially suitable for placing in veins and other channels where only a small pressure is exerted against the wall of the channel. In FIG. 11 the valve 6 is mounted at the end of the tubular means 24. In FIG. 12 an embodiment is shown where the valve 6 is mounted in a central position in the tubular means 24.

An explanation of a method of implanting a valve prosthesis according to the invention is given below:

- a valve prosthesis 9 made of a stent 1 and a collapsible valve 6, as described above, is placed on a deflated balloon means and is manually compressed thereon,
- the balloon means 13 and the valve prosthesis are drawn into an insertion cover 11A,
- a guide wire 18 is inserted into the left ventricle of the heart through the central opening 17 of the balloon catheter under continuous fluoroscopi,
- the insertion cover 11A conveys the guide wire 18 to a point in the channel in the immediate vicinity of the desired position of the valve prosthesis,
- the balloon means 13 is pushed out of the protection cap 11A and the valve prosthesis is positioned in the desired position if necessary by use of further registration means to ensure an accurate positioning,
- the balloon means 13 is inflated with a certain overstretching of the channel,
- the balloon means 13 is deflated, and
- the balloon means 13, the guide wire 18 and the protection cap 11A are drawn out and the opening in the channel, if any, wherein the valve prosthesis is inserted can be closed.

FIGS. 13-14 are perspective view illustrating two further embodiments of a stent without a valve. In FIG. 13, the stent 100 is made by support means in the form of helical wires 102, 103, with loops 104 and circumferentially expandable sections 125. Each of the two helical wires 102, 103 is bent to form rings 107, 108. In FIG. 14, the stent 200 is made by support means in the form of gate-shaped wires 202, 203, with loops 204 and circumferentially expandable sections 225. Each of the two gate-shaped wires 202, 203 is bent to form rings 207, 208. The primary difference between prior described embodiments, such as in FIG. 2, versus those embodiments shown in FIGS. 13 and 14, for example, is the replacement of the series of loops 4 (FIG. 2) with the helical wires 102, 103 and loops 104 (FIG. 13) or the grate-shaped wires 202, 203 and loops 204 (FIG. 14). As the artisan will readily appreciate, the embodiments of FIGS. 13-14 otherwise include those features shown in prior described embodiments, such as in FIG. 2, including the commissural points 5 forming commissural supports.

What is claimed is:

1. A valve prosthesis for implantation in a body, comprising:
    an elastical stent comprising a cylindrical support having circumferentially expandable sections comprised of a series of loops with commissural supports therebetween and integral therewith; and
    an elastical valve, commissural points of which are mounted on a respective one of the commissural supports;
    wherein the cylindrical support is radially collapsible for implantation in the body via a catheter.

2. The valve prosthesis according to claim 1 wherein:
    the elastical valve comprises a biologically tribolate valve.

3. The valve prosthesis according to claim 1, wherein:
    the elastical valve comprises a cardiac valve.

4. The valve prosthesis according to claim 1, wherein:
    the elastical valve comprises a venous valve.

5. The valve prosthesis according to claim 1, wherein:
    the cylindrical support comprises a metal having a stiffness sufficient to prevent a contraction of the cylindrical support of more than about 10% following expansion.

6. The valve prosthesis according to claim 1, wherein:
    the cylindrical support comprises a thread structure which forms a cylinder surface.

7. A valve prosthesis for implantation in a body, comprising:
    an elastical stent comprising a support means having circumferentially expandable sections comprised of a series of loops with commissural supports therebetween and integral therewith; and
    an elastical valve, commissural points of which are mounted on a respective one of the commissural supports;
    wherein the support means is radially collapsible for implantation in the body via a catheter and the support means extends axially for supporting the elastical valve.

8. The valve prosthesis according to claim 7, wherein:
    the support means is cylindrical.

9. The valve prosthesis according to claim 7, wherein:
    a surface of the support means is cylindrical.

10. The valve prosthesis according to claim 7, wherein:
    the elastical valve is a biologically trilobate valve.

11. The valve prosthesis according to claim 7, wherein:
    the support means is expandable upon removal from the catheter.

12. The valve prosthesis according to claim 7, wherein:
    the elastical valve comprises a cardiac valve.

13. The valve prosthesis according to claim 7, wherein:
    the elastical valve comprises a venous valve.

14. The valve prosthesis according to claim 7, wherein:
    the support means comprises a metal having a stiffness sufficient to prevent a contraction of the support means of more than about 10% following expansion.

15. A valve prosthesis for implantation in a body, comprising:
    an elastical stent comprising a cylindrical support having a thread structure cylinder surface; and
    an elastical valve, commissural points of which are mounted on the cylinder surface; and
    wherein the cylinder surface is radially collapsible for implantation in the body via a catheter,
    the thread structure comprises stainless steel wire folded in a plurality of loops, bended according to a circle, and welded to provide at least two closed rings,
    the at least two closed rings are mutually connected end to end to form the cylindrical support, and three loops in an external one of the rings are folded with a greater height than remaining ones of loops to form apices.

16. The valve prosthesis according to claim 15, wherein:
the cylindrical support is expandable upon removal from the catheter;
each of the closed rings comprises a wire having a diameter of 0.55 mm;
a height of the remaining ones of loops is approximately 8 mm;
a height of the three greater height loops is approximately 14 mm; and
the cylindrical support and the elastical valve mounted thereon, when collapsed, have an outer diameter of approximately 10 mm and, when expanded, an outer diameter of approximately 30 mm.

17. The valve prosthesis according to claim 15, wherein:
the stent is made to be fixed, through expansion of the cylindrical support upon removal from the catheter, at one point in a channel in which the valve prosthesis is implanted, which point is different from a point where the elastical valve is mounted on the stent.

18. A valve prosthesis for implantation in a patient's body without requiring open heart surgery, comprising:
a self expandable stent constructed to be radially compressible and re-expandable, the stent having a top end, a bottom end and a metallic outer surface configured to contact native tissue in a body channel; and
a collapsible and re-expandable elastical valve comprising three flaps formed entirely of biological tissue, the elastical valve positioned within an interior portion of the stent for folding and expanding together with the stent, the elastical valve located between the top and bottom ends of the stent, the elastical valve having three commissural points sutured to the self expandable stent, the elastical valve configured to allow blood to flow in one direction such that blood is capable of flowing through the stent from the bottom end toward the top end;
wherein the valve prosthesis is radially compressible from an expanded condition to a compressed condition, the compressed condition having a first outer diameter of 10 mm or less for insertion inside a tubular wall of a cap along a distal end portion of a delivery catheter for advancement through a small inlet opening into the body channel and wherein the valve prosthesis is radially self-expandable upon ejection from the cap to a re-expanded condition comprising a second outer diameter of approximately 27 mm or more such that the second outer diameter of the valve prosthesis is greater than an inner diameter of the body channel for securing the valve prosthesis in the body channel without suturing the valve prosthesis to native tissue and to establish valvular function in the body channel, thereby allowing implantation of the valve prosthesis in the body channel for replacing the function of a natural aortic valve in an adult human being without open heart surgery and wherein the valve prosthesis is detachable from the delivery catheter such that the delivery catheter can be removed from the body channel and the small inlet opening can be closed such that the patient can resume a substantially normal life.

19. The valve prosthesis according to claim 18, wherein:
the self-expandable stent has a height comprising a first range configured to be positioned downstream of the coronary ostia and a second range configured to support the elastical valve between the coronary ostia and the left ventricle.

20. The valve prosthesis according to claim 19, wherein:
the elastical valve is formed entirely of biological tissue from a pig heart.

21. The valve prosthesis according to claim 18, wherein:
the elastical valve comprises a venous valve.

22. The valve prosthesis according to claim 18, wherein:
the stent has a stiffness sufficient to prevent a contraction of more than about 10% following re-expansion.

23. The valve prosthesis according to claim 18, wherein:
the stent comprises a grate shaped structure which forms a cylinder surface.

24. A valve prosthesis configured to be implanted in a body channel without open heart surgery for replacing the function of a natural aortic valve in an adult human being, comprising:
a radially compressible and re-expandable metallic stent having a top end, a bottom end and a metallic outer surface configured to directly contact surrounding native tissue in a body channel with a pressure sufficient to prevent detachment from the body channel; and
a radially collapsible and re-expandable valve positioned within an interior portion of the stent and sutured to the stent for folding and expanding together with the stent, the valve having three flaps formed of biological tissue from a pig, the three flaps positioned between the top and bottom ends of the stent for allowing blood to flow in one direction such that blood is capable of flowing through the stent from the bottom end toward the top end, the valve having three commissural points sutured to the stent;
wherein the valve prosthesis is radially compressible from an expanded condition to a compressed condition, the compressed condition having an outer diameter of less than 12.5 mm to be located inside a tubular wall of a cap along a distal end portion of a catheter for advancement through a small inlet opening into the body channel and wherein the valve prosthesis is radially re-expandable upon ejection from the cap to a re-expanded condition comprising an outer diameter of approximately 27 mm or larger for securing the valve prosthesis to the surrounding native tissue without suturing the valve prosthesis to the surrounding native tissue and wherein the valve prosthesis is detachable from the catheter such that the catheter can be removed from the body channel and the small inlet opening can be closed and wherein the metallic stent has a sufficient height such that the top end of the stent is capable of being positioned downstream of the coronary ostia while the valve is positioned substantially between coronary ostia and a left ventricle of a heart for replacing the function of the natural aortic valve without open heart surgery.

25. The valve prosthesis according to claim 24, wherein:
at least a portion of the metallic stent is substantially cylindrical.

26. The valve prosthesis according to claim 24, wherein:
the metallic stent is self-expandable upon ejection from the cap and wherein the outer diameter in the re-expanded condition is slightly larger than an inner diameter of the body channel.

27. The valve prosthesis according to claim 24, wherein:
the radially collapsible and re-expandable valve comprises a cardiac valve.

28. The valve prosthesis according to claim 24, wherein:
the radially collapsible and re-expandable valve comprises a venous valve.

29. The valve prosthesis according to claim 24, wherein:
the metallic stent comprises a grate shaped structure having a stiffness sufficient to prevent a contraction of the metallic stent of more than about 10% following re-expansion.

30. A valve prosthesis for replacing the function of a native valve in a patient's body by a technique of catheterization, comprising:
a radially collapsible and re-expandable stent having a top end, a bottom end and a metallic outer surface configured to contact native tissue in a body channel; and
a collapsible and re-expandable valve structure positioned within an interior portion of the stent and sutured to the stent, the valve structure having three flaps formed entirely of biological tissue, the three flaps positioned between the top and bottom ends of the stent, the valve structure having three commissural points sutured to the stent, the valve structure configured to allow blood to flow in one direction such that blood enters through a bottom opening at the bottom end of the stent and exits through a top opening at the top end of the stent;
wherein the valve prosthesis is radially collapsible to an outer diameter of less than 10 mm for introduction by way of a catheter through an inlet opening into the body channel and wherein the outer diameter of the stent is radially re-expandable to a re-expanded dimension sized to engage the native tissue in the body channel with a pressure sufficient for preventing detachment from the body channel and for fixing the valve prosthesis in the body channel without suturing the valve prosthesis to native tissue and wherein the valve prosthesis is detachable from the catheter such that the catheter can be removed from the patient's body and the inlet opening can be closed while the valve prosthesis remains in the body channel;
wherein the valve structure has an expanded outer diameter in the range of about 25 to 27 mm.

31. A valve prosthesis for replacing the function of a native valve in a patient's body by a technique of catheterization, comprising:
a radially collapsible and re-expandable stent having a top end, a bottom end and a metallic outer surface configured to contact native tissue in a body channel; and
a collapsible and re-expandable valve structure positioned within an interior portion of the stent and sutured to the stent, the valve structure having three flaps formed entirely of biological tissue, the three flaps positioned between the top and bottom ends of the stent, the valve structure having three commissural points sutured to the stent, the valve structure configured to allow blood to flow in one direction such that blood enters through a bottom opening at the bottom end of the stent and exits through a top opening at the top end of the stent;
wherein the valve prosthesis is radially collapsible to an outer diameter of less than 10 mm for introduction by way of a catheter through an inlet opening into the body channel and wherein the outer diameter of the stent is radially re-expandable to a re-expanded dimension sized to engage the native tissue in the body channel with a pressure sufficient for preventing detachment from the body channel and for fixing the valve prosthesis in the body channel without suturing the valve prosthesis to native tissue and wherein the valve prosthesis is detachable from the catheter such that the catheter can be removed from the patient's body and the inlet opening can be closed while the valve prosthesis remains in the body channel;
wherein the re-expanded dimension has a diameter of about 30 mm.

32. A valve prosthesis for replacing the function of a natural heart valve, comprising:
a radially compressible and re-expandable stent, the stent being compressible from an expanded condition to a compressed condition having an outer diameter suitable for introduction through a small inlet opening into a body channel by way of a delivery catheter and the stent being re-expandable to a re-expanded condition, the stent having a metallic outer surface for contacting surrounding tissue in the body channel, wherein an outer diameter of the stent in the re-expanded condition is at least 2.7 times larger than the outer diameter of the stent in the compressed condition; and
a collapsible and re-expandable valve structure mounted to the stent for folding and expanding together with the stent, the valve structure having three commissural points coupled to the stent, the valve structure having three flaps formed entirely of biological tissue, the valve structure positioned within an interior portion of the stent for preventing blood flow in one direction;
wherein the valve prosthesis is detachable from the delivery catheter after deployment in the body channel such that the delivery catheter can be removed from the body channel and the small inlet opening can be closed and wherein the stent has a stiffness in the expanded condition, the stiffness being sufficient to maintain pressure along surrounding tissue in the body channel for securing the valve prosthesis and preventing detachment from the body channel, thereby allowing the valve prosthesis to be permanently implanted in the body channel by way of catheterization without requiring surgical intervention.

33. The valve prosthesis according to claim 32, wherein:
the stent is balloon expandable.

34. The valve prosthesis according to claim 32, wherein:
the stent is formed of a metallic self-expandable material.

35. The valve prosthesis according to claim 34, wherein:
the self-expandable stent has a height comprising a first range configured for fixation in the ascending aorta downstream of the coronary ostia and a second range configured to position the valve structure substantially between the coronary ostia and the left ventricle after implantation.

36. The valve prosthesis of claim 32, wherein:
the valve structure is formed entirely of biological tissue from a slaughtered pig.

37. The valve prosthesis of claim 32, wherein:
the valve prosthesis is configured to be implanted in the body channel without opening the thoracic cavity.

38. A valve prosthesis configured for implantation without surgical intervention for replacing the function of a defective natural valve in an adult human heart, comprising:
a compressible and re-expandable stent having an inlet end, an outlet end and a metallic outer surface, the stent being radially compressible from an expanded state to a compressed state for introduction through an inlet opening into a body channel by way of a catheter, the stent being re-expandable to a re-expanded state such that the metallic outer surface engages surrounding tissue in the body channel, wherein an outer diameter of the stent in the re-expanded state is at least 2.7 times larger than an outer diameter of the stent in the compressed state; and
a collapsible and re-expandable valve structure mounted within an interior portion of the stent between the inlet and outlet ends of the stent for folding and expanding together with the stent and configured for preventing blood flow in one direction, the valve structure having movable flaps positioned between the inlet and outlet ends of the stent for allowing blood to flow only from the inlet end toward the outlet end of the stent;

wherein stent stiffness provides the sole means of fixation to surrounding tissue for securing the valve prosthesis to the body channel and wherein the valve prosthesis is detachable from the catheter such that the catheter can be removed from the body channel after deploying the valve prosthesis in the body channel and the inlet opening can be closed such that the valve prosthesis is permanently implantable in the body channel for replacing the function of a native valve without suturing the valve prosthesis to surrounding native tissue.

39. The valve prosthesis of claim 38, wherein:
the stent comprises a grate-shaped structure.

40. The valve prosthesis of claim 39, wherein:
the stent is self expandable.

41. The valve prosthesis of claim 40, wherein:
the stent further comprises an outlet end portion configured for fixation in the ascending aorta at a location downstream of the coronary ostia and an inlet end portion configured for positioning the valve structure substantially between the coronary ostia and the left ventricle.

42. The valve prosthesis of claim 41, wherein:
at least the inlet end portion of the stent is substantially cylindrical.

43. The valve prosthesis of claim 38, wherein:
the valve structure is formed of biological tissue before the valve prosthesis is introduced through the inlet opening into the body channel.

44. The valve prosthesis of claim 43, wherein the biological tissue forms two or more adjacent flaps, the flaps forming commissural points between adjacent flaps.

45. The valve prosthesis of claim 38, wherein:
the outer diameter of the stent in the re-expanded state is at least three times larger than the outer diameter of the stent in the compressed state.

46. A valve prosthesis configured for implantation in an adult human being without requiring surgical intervention for replacing the function of a defective natural aortic valve, comprising:

a self expandable metallic stent having an inlet end, an outlet end and a metallic outer surface, the stent being radially compressible to a compressed condition having an outer diameter suitable for insertion into a protection cap and sized for introduction through an inlet opening into a body channel by way of a catheter, the stent configured to self-expand to an expanded condition upon ejection from the protection cap, the stent comprising an outer diameter in the expanded condition at least three times greater than the outer diameter in the compressed condition, the outer diameter being greater than an inner diameter of an ascending aorta such that at least a portion of the metallic outer surface of the stent engages an inner wall of the ascending aorta for counteracting detachment of the valve prosthesis;

a collapsible and expandable elastical valve comprising three flaps formed of biological tissue, the elastical valve positioned within an interior portion of the stent for folding and expanding together with the stent, the elastical valve located between the inlet and outlet ends of the stent, the elastical valve having three commissural points sutured to the self expandable stent, the elastical valve configured to allow blood to flow in one direction such that blood is capable of flowing through the stent from the inlet end toward the outlet end;

wherein the valve prosthesis is detachable from the catheter such that the catheter can be removed from the body channel after implanting the valve prosthesis and the inlet opening can be closed such that the valve prosthesis is permanently implantable for replacing the function of the defective natural aortic valve without suturing the valve prosthesis to surrounding native tissue.

47. The valve prosthesis according to claim 46, wherein:
the self-expandable stent comprises an inlet end portion configured to position the elastical valve substantially between the coronary ostia and the left ventricle.

48. The valve prosthesis according to claim 46, wherein:
the outer diameter of the stent in the compressed condition is 10 mm or less.

49. The valve prosthesis according to claim 48, wherein:
the outer diameter of the stent in the expanded condition is 30 mm or greater.

* * * * *

(12) INTER PARTES REEXAMINATION CERTIFICATE (657th)
United States Patent
Andersen et al.

(10) Number: US 7,618,446 C1
(45) Certificate Issued: *Jul. 29, 2013

(54) VALVE PROSTHESIS FOR IMPLANTATION IN THE BODY AND A CATHETER FOR IMPLANTING SUCH VALVE PROSTHESIS

(75) Inventors: Henning Rud Andersen, Hoejbjerg (DK); John Michael Hasenkam, Aarhus (DK); Lars Lyhne Knudsen, Aarhus (DK)

(73) Assignee: Edwards Lifesciences AG, St.-Prex (CH)

Reexamination Request:
No. 95/001,616, May 4, 2011

Reexamination Certificate for:
Patent No.: 7,618,446
Issued: Nov. 17, 2009
Appl. No.: 10/268,253
Filed: Oct. 10, 2002

( * ) Notice: This patent is subject to a terminal disclaimer.

Related U.S. Application Data

(60) Continuation of application No. 09/514,426, filed on Feb. 28, 2000, now Pat. No. 6,582,462, which is a continuation of application No. 09/026,574, filed on Feb. 20, 1998, now Pat. No. 6,168,614, which is a continuation of application No. 08/955,228, filed on Oct. 21, 1997, now abandoned, which is a division of application No. 08/801,036, filed on Feb. 19, 1997, now Pat. No. 5,840,081, which is a continuation of application No. 08/569,314, filed on Dec. 8, 1995, now abandoned, which is a continuation of application No. 08/352,127, filed on Dec. 1, 1994, now abandoned, which is a division of application No. 08/261,235, filed on Jun. 14, 1994, now Pat. No. 5,411,552, which is a continuation of application No. 07/961,891, filed as application No. PCT/DK91/00134 on May 16, 1991, now abandoned.

(30) Foreign Application Priority Data

May 18, 1990 (DK) .................................... 1246/90

(51) Int. Cl.
*A61F 2/24* (2006.01)
*A61F 2/90* (2013.01)
*A61F 2/88* (2006.01)

(52) U.S. Cl.
USPC ........................................ 623/1.26; 623/2.14

(58) Field of Classification Search
None
See application file for complete search history.

(56) References Cited

To view the complete listing of prior art documents cited during the proceeding for Reexamination Control Number 95/001,616, please refer to the USPTO's public Patent Application Information Retrieval (PAIR) system under the Display References tab.

*Primary Examiner* — Catherine S. Williams

(57) ABSTRACT

A valve prosthesis for implantation in the body by use of a catheter includes a stent made from an expandable cylinder-shaped thread structure including several spaced apices. The elastically collapsible valve is mounted on the stent as the commissural points of the valve are secured to the projecting apices. The valve prosthesis can be compressed around balloons of the balloon catheter and inserted in a channel, for instance, in the aorta. When the valve prosthesis is placed correctly, the balloons are inflated to expand the stent and wedge it against the wall of the aorta. The balloons are provided with beads to ensure a steady fastening of the valve prosthesis on the balloons during insertion and expansion. The valve prosthesis and the balloon catheter make it possible to insert a cardiac valve prosthesis without a surgical operation involving opening the thoracic cavity.

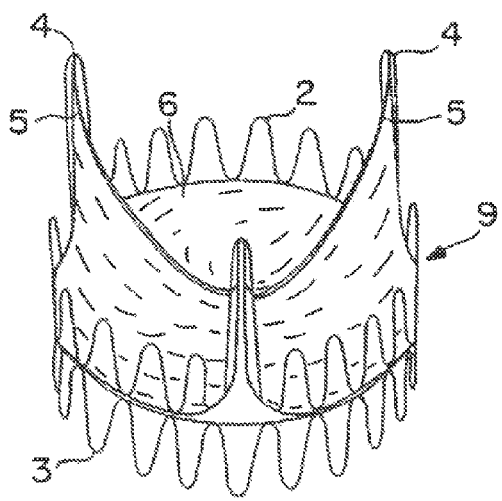

INTER PARTES REEXAMINATION CERTIFICATE ISSUED UNDER 35 U.S.C. 316

THE PATENT IS HEREBY AMENDED AS INDICATED BELOW.

AS A RESULT OF REEXAMINATION, IT HAS BEEN DETERMINED THAT:

Claims 18-49 are cancelled.

Claims 1-17 were not reexamined.

\* \* \* \* \*